United States Patent [19]

Moreau et al.

[11] Patent Number: 5,454,267

[45] Date of Patent: Oct. 3, 1995

[54] MULTI-ELEMENT ULTRASONIC PROBE FOR ELECTRONIC SCANNING

[75] Inventors: Georges Moreau, Viriat; Jacques Archer, Chatenay Malabry; Francis Bodson, Givry; Olivier Burat, Saint Remy, all of France

[73] Assignee: Framatome, Courbevoie, France

[21] Appl. No.: 811,683

[22] Filed: Dec. 23, 1991

[30] Foreign Application Priority Data

Dec. 21, 1990 [FR] France .................... 90 16155

[51] Int. Cl.⁶ .................... G01N 29/10; G01N 29/24
[52] U.S. Cl. .................... 73/623; 73/622; 73/626; 73/640; 73/641
[58] Field of Search ............ 73/620, 622, 623, 73/625, 628, 633, 640, 641, 642, 626

[56] References Cited

U.S. PATENT DOCUMENTS

| 3,693,415 | 9/1972 | Whittington | 73/622 |
| 5,125,274 | 6/1992 | Gilbert | 73/623 |

FOREIGN PATENT DOCUMENTS

| 333552 | of 0000 | European Pat. Off. . | |
| 2901231 | of 0000 | Germany . | |
| 2806550 | 8/1979 | Germany | 73/622 |
| 0039460 | 4/1981 | Japan | 73/622 |
| 0316005 | 11/1971 | U.S.S.R. | 73/622 |
| 1552897 | of 0000 | United Kingdom . | |
| 2208138 | of 0000 | United Kingdom . | |

OTHER PUBLICATIONS

Search Report FR 9016155.

Abstracts vol. 8, No. 169 "Automatic Ultrasonic Flaw Detector".

"Images of the Twenty–First Century" IEEE Engineering in Medicine and Biology Society.

Primary Examiner—Hezron E. Williams
Assistant Examiner—Rose M. Finley
Attorney, Agent, or Firm—Pollock, Vande Sande & Priddy

[57] ABSTRACT

The ultrasonic transducer (5) is moved along the axial direction of elements of elongate shape (1), and is electrically excited for the emission of ultrasonic waves. Electrical measurement currents originating from the transducer (5) are collected and analyzed. The transducer (5) comprises a support having a concave active surface having curved generatrices and a plurality of piezoelectric elements fixed to the active surface of the support in adjacent dispositions.

18 Claims, 5 Drawing Sheets

MULTI-ELEMENT ULTRASONIC PROBE FOR ELECTRONIC SCANNING

FIELD OF THE INVENTION

The invention relates to a device for ultrasonic non-destructive inspection of elements of elongate shape having a substantially constant cross-section and more particularly for inspecting the wall of elongated tubes of small or large diameter, long length tubes and of solid or hollow structural sections.

BACKGROUND OF THE INVENTION

As regards small diameter tubes, the heat exchangers such as steam generators, in particular steam generators used in power-generating nuclear power stations, generally comprise a bundle of long length tubes which may be straight, bent or even helically coiled.

In particular, in the case of nuclear reactors cooled by pressurized water or by liquid sodium, the bundle of tubes is disposed inside an external cylindrical enclosure having a vertical axis, and the tubes are fixed, by their terminal portions, either to tube plates integral with the enclosure or to tube plates or manifolds exterior to the enclosure of the steam generator. In the latter case, each tube comprises an intermediate fastening, via a thermal sleeve, to the enclosure.

The fluid cooling the reactor flows either inside or outside the tubes of the bundle so as to heat and vaporize feedwater through their wall.

The walls of the tubes which constitute the heat exchange tubes therefore separate a fluid cooling the nuclear reactor from the feedwater to be vaporized.

In the case of nuclear reactors cooled by pressurized water, the fluid cooling the reactor, i.e., the primary coolant, comes into contact, inside the reactor vessel, with the core of the reactor constituted by the fuel assemblies, and is therefore liable to contain radioactive products. It is therefore essential to work under conditions such that, during manufacture and use of the steam generators, any leakage of the fluid cooling the reactor towards the feedwater which, after conversion to steam goes to the turbine, is avoided.

Likewise, in the case of fast neutron nuclear reactors cooled by a reactive metal such as liquid sodium, it is necessary to avoid any leakage through the wall of the exchange tubes being manifested by water or water vapor coming into contact with the liquid sodium and by an extremely vigorous reaction which can lead to explosions and to damage, at least in part, of the steam generator.

It is therefore necessary to carry out meticulous inspections of the wall of the heat exchange tubes at different stages of the manufacture of the steam generators, and after a certain time in use of these steam generators, in order to ensure complete integrity of the wall of these tubes separating the heat exchange fluids.

As regards larger diameter tubes, the device may be applied to the inspections of the walls and of the welds of the tubes conveying fluids such as hydrocarbons (pipeline), gases or any other fluids.

In general, it may be necessary to inspect the state of the wall of tubes during their manufacture, before or after their mounting and during periodic inspections, for example after a certain operation time of apparatuses or systems for which these tubes are used. It may also be necessary to inspect the state of the tubular walls of long length lines such as pipelines.

The tubes used in the apparatuses, or in the systems connecting apparatuses, or in the fluid-flow lines, may experience elevated temperatures and possibly high pressures.

As regards solid or hollow structural sections, it may be necessary to carry out the inspection of solid bars of circular or prismatic cross-section, or more especially of the rails for moving machinery or any element of elongate shape having a substantially constant transverse cross-section.

The purpose of the non-destructive inspections carried out on the tubes and structural sections may be to check that their integrity conforms to that required in construction or to reveal defects appearing in operation.

In order to carry out these inspections, it has been proposed to use various methods employing, for example, eddy current probes or radiographic examination techniques.

The devices used in employing these methods are generally bulky, so that it may be difficult, if not impossible, to cause them to pass at least into certain portions of the tubes, for example into the bent portions having a small bend radius. These techniques may also be completely inapplicable in the case of small diameter heat exchanger tubes.

In the case of steam generators associated with nuclear reactors, the exchange tubes may have an internal diameter less than 20 mm and a length of the order of 50 to 100 m.

Furthermore, eddy current methods have a reduced sensitivity in the detection of the defects of the welds of the tubes and in the inspection of ferromagnetic materials.

The deposits which may be present inside or outside the tubes, deposits which may be metallic and, for example, constituted by solidified sodium in the case of fast neutron steam generators and heat exchangers, are liable to interfere with the signal corresponding to the eddy currents and to decrease strongly the sensitivity of the detection.

The use of non-destructive inspection methods employing ultrasound has enabled some of the abovementioned drawbacks to be avoided, in the case of the inspection of small diameter tubes.

It has been proposed to use ultrasonic transducers emitting an ultrasonic beam in the direction of the wall of the tube to be inspected, i.e., in a radial plane. It is possible to associate with these transducers, mechanisms enabling the ultrasonic beam to be made to scan mechanically the tube in the circumferential direction or along a helix.

In order to carry out a non-destructive inspection of the wall of a tube, via the inside or via the outside of the tube, by circumferential or helical scanning, it has been proposed to use a device comprising an ultrasonic probe or transducer which may be translationally moved along the axial direction of the tube and which may be rotated about an axis coincident with the axis of the tube during the inspection.

The ultrasonic beam produced by the transducer may be emitted directly in the direction of the wall of the tube or reflected towards the wall by a mirror.

Such devices have the drawback of requiring the use of complex mechanisms such as fractional horsepower motors and speed-reducing gears enabling the transducer, and, possibly the mirror, to be rotatably driven, mechanical linkage means comprising small-size universal joints or even rotating commutators.

The mechanisms enabling the transducer and the motor to rotate are tricky to operate and may be sensitive to the presence of solid particles detached from the wall of the tube and which may be in suspension in the coupling fluid.

Because of the design of the transducer, the angle of incidence of the ultrasonic beam and the focal distance of this beam are fixed unless it is intended to use a mirror of complex shape or which is moved in a specially adapted manner.

Finally, such devices have a significant bulkiness in the longitudinal and/or diametral direction of the tube.

There are also known devices for ultrasonic inspection of small diameter tubes comprising a non-rotating transducer constituted by several piezoelectric elements placed in a single plane, juxtaposed or separated by insulation parts, so as to constitute an array which is symmetrical in revolution and in which each of the piezoelectric elements is capable of emitting an ultrasonic beam forming separate impact zones in the plane. Each beam makes it possible to analyze a specified impact zone of the tube, and the array of the beams emanating from the piezoelectric elements of a single plane does not therefore permit a complete analysis of the circumference of the tube.

The circumferential analysis of the wall of the tube by these points of impact is obtained by excitation, in a successive manner and in a given order, of each of the piezoelectric elements. However, taking into account the bulkiness of the elements, the points of impact of the beams constituting focal spots on the wall of the tube are relatively far apart in the emission plane of the transducer.

To increase the number of these points of impact, piezoelectric elements disposed along several rows and in staggered positions are used.

However, in this case, the drawbacks of the conventional-type transducers are encountered again. In particular, the angle of incidence of the beam and the focal distance of the ultrasonic waves are not modifiable. The device may be bulky in the longitudinal direction because it is necessary to use several rows of transducers spaced in the axial direction. Furthermore, while using the transducer, it is necessary to prevent any radial movement during its movement in the axial direction of the tube, so as not to lose the angular reference of the points examined.

In fact, the devices according to the prior art are generally bulky and cannot be used over the entire length of small diameter tubes having a significant length which can reach 100 mm and which are bent with small bend radii.

U.S. Pat. No. 3,693,415 discloses a scanning ultrasonic inspection method and device for the detection of cracks in a part such as a tube, in which transducers are disposed along a row around the part and are supplied by successive groups, so as to focus an ultrasonic beam onto successive points of the part during inspection. This method makes it possible to obtain a narrow focal spot in the circumferential direction of a tube during examination. However, in the axial direction of the tube, along which the transducers have a certain length, the focal spot extends over a length greater than the length of the transducers because of the divergence of the ultrasonic beam. This focal spot therefore has the shape of a "thick line". The resolution of the inspection device is therefore limited and it is not possible to detect cracks of small size.

SUMMARY OF THE INVENTION

The object of the invention is therefore to propose a device for ultrasonic non-destructive inspection of elements of elongate shape having a substantially constant cross-section, comprising an ultrasonic transducer comprising a support having an active surface whose shape corresponds to the shape of the surface of the elongate element, which surface faces the surface of the elongate element during the movements of the transducer, and a plurality of piezoelectric elements fixed to the active surface of the support in adjacent dispositions, means for moving the transducer along the longitudinal direction of the element of elongate shape, means for electrical excitation of the transducer for the emission of ultrasonic waves in the direction of at least one surface of the element of elongate shape, which excitation means are connected to the piezoelectric elements and controlled so as to produce sequential excitation and scanning over the surface and/or in the depth of the element of elongate shape in at least one direction, and means for collecting and analyzing electrical measurement currents originating from the transducer, this device enabling an inspection of the wall or of the volume of the elongate element to be performed with an excellent resolution and defects such as cracks of very small size to be detected.

For this purpose, the support of the transducer comprises a concave active surface whose cross-section through a plane passing through the axis of the transducer, coincident with the longitudinal axis of the element of elongate shape, is a curve whose concavity is directed towards the element of elongate shape, the piezoelectric elements being disposed along successive axial curves of the active surface of the support of the transducer, so as to enable the ultrasonic waves to be focused in the axial direction, i.e. in the direction of the axis of the element of elongate shape.

In the case of the inspection of tubes and particularly of small diameter, long length tubes, the transducer of the device according to the invention comprises a support having an active surface which is symmetrical in revolution and has curved generatrices and a plurality of piezoelectric elements disposed along generatrices of the active surface in successive angular positions about the axis of the active surface of the support which are spaced apart by less than 20° and preferably less than 10° in the case of small diameter tubes, and the means for exciting the piezoelectric elements are sequentially controlled so as to obtain a scanning of the wall of the tube by ultrasonic waves, at least in the circumferential direction.

BRIEF DESCRIPTION OF THE DRAWINGS

So as to make the invention well understood, there will now be described, by way of example and with reference to the attached drawings, several embodiments of an ultrasonic inspection device according to the invention and its use for the non-destructive inspection of small diameter, long length tubes, of large diameter tubes and of structural-section elements such as rails.

DESCRIPTION OF THE PREFERRED EMBODIMENT

Figure 1:
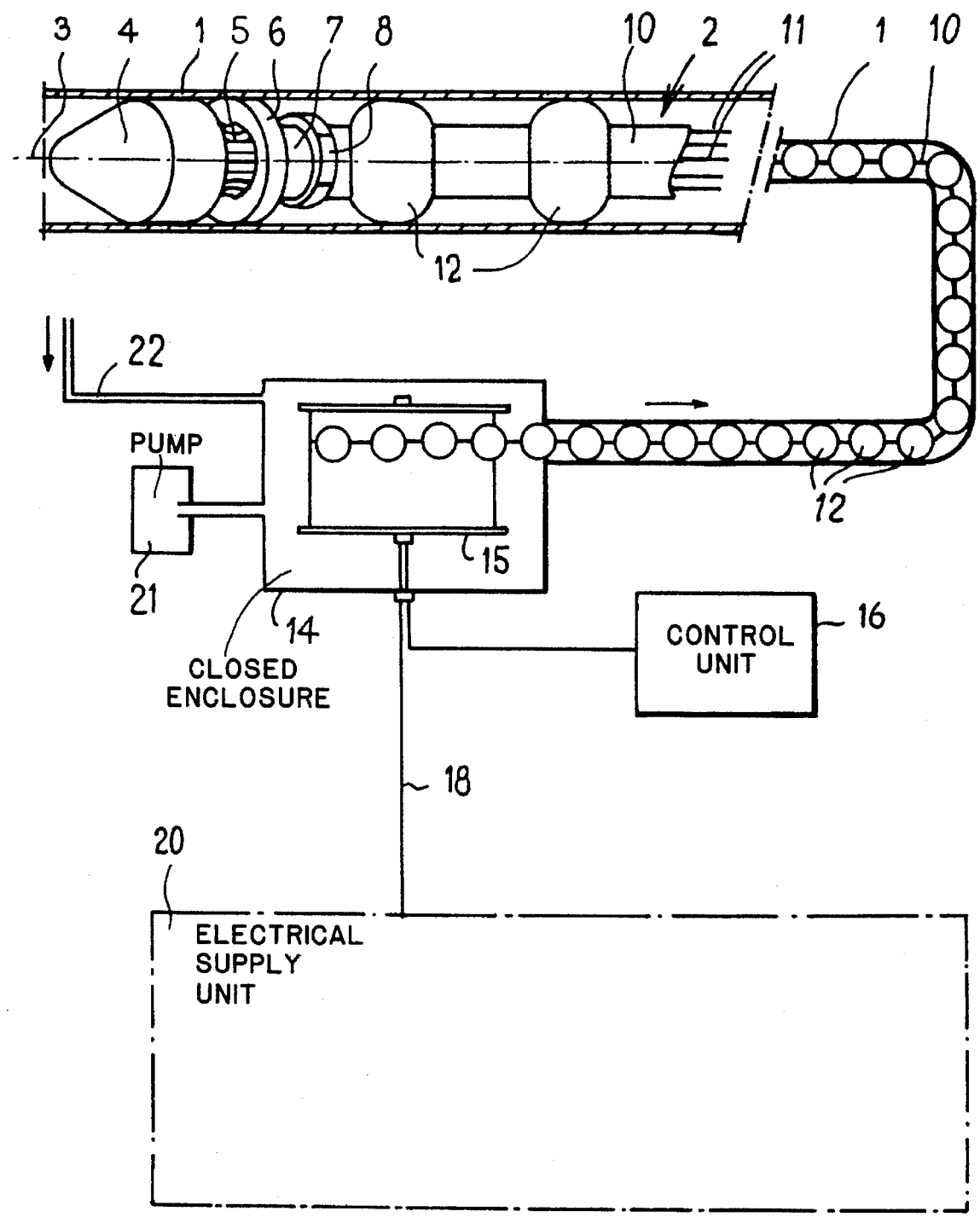
FIG. 1 is an overall view of an ultrasonic non-destructive inspection device according to the invention whose transducer is in an operating position inside a tube.

FIG. 1, shows a device for ultrasonic non-destructive inspection of the wall of a tube 1 having a small diameter, for example less than 20 mm and which may have a long length, for example of the order of several tens of meters.

The device according to the invention comprises a movable portion 2 which may be moved inside and along the direction of the axis 3 of the tube 1.

Figure 2:
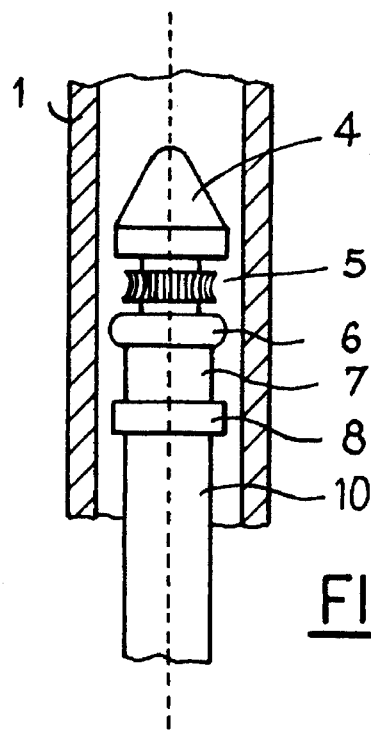
FIG. 2 is an elevation, in cross-section of a portion of an inspection device according to the invention inserted into a tube being inspected.

The movable portion 2 comprises a front end which is engaged firstly in the tube 1 to be inspected and which is shown in the upper portion of FIG. 1 and in FIG. 2.

The front portion of the movable entirety of the inspection device comprises successively, from the front to the rear, a guiding head 4, an ultrasonic transducer 5, a guiding ring 6, a pre-amplifier and multiplexer device 7 providing the switching of sensitive elements of the transducer 5, and an electrical connection ring 8.

The front portion 2 of the inspection device is fixed to the end of a flexible cable 10 constituting the portion by means of which the transducer 5 moves translationally inside the tube.

The guiding head 4 is constituted by a solid body symmetrical in revolution which may have the shape of a cone with a rounded apex or the shape of a hemisphere. The maximum diameter of the guiding head 4 and of the ring 6 are smaller than the inner diameter of the tube 1 to be inspected but are greater than the outer diameter of the ultrasonic transducer 5.

The cable 10 has a tubular construction so as to permit the passage, in its internal borehole and along its entire length, of electrical conductors 11 enabling the transducer 5 to be supplied with electrical current and the measurement signals originating from the transducer 5 to be collected by means of the connection ring 8.

The cable 10 comprises guiding elements 12 radially projecting over its external surface and preferably having a toric or spherical shape. The outer diameter of the guiding elements 12 is slightly less than the inner diameter of the tube 1, so as to obtain an effective guiding of the movable portion 2 of the inspection device inside the tube 1 during its axial movements and to allow the passage of coupling fluid.

The inspection device according to the invention also comprises, inside a closed enclosure 14 connected in a leaktight manner to the inlet end of the tube 1, a device 15 for translationally moving the cable 10 of the movable portion 2. The device 15 may be a pull-push device comprising a winch for reeling and unreeling the cable 10 and may be rotatably driven at a controlled speed, inside the enclosure 14, by means of a shaft connected to a motor controlled by a control unit 16.

The conductors 11 for supplying the transducer 5 with electrical current and for collecting the electrical measurement signals from the transducer are connected electrically to conductors of a cable 18 supplying the transducer and collecting the signals, for example by means of a commutator associated with the winch 15.

The cable 18 is connected to a unit 20 comprising means for supplying the transducer with electrical current and means for collecting and analyzing the measurement signals originating from the transducer.

A circulating pump 21 is connected via a pipe to the internal volume of the enclosure 14 and provides the flow of a coupling liquid such as water inside the tube 1, so that this coupling liquid reaches the level of the transducer 5 regardless of its position inside the tube 1.

A return pipe 22 for the coupling liquid is also connected to the enclosure 14. Thus, a continuous flow of coupling liquid is provided inside the tube.

Figure 3:
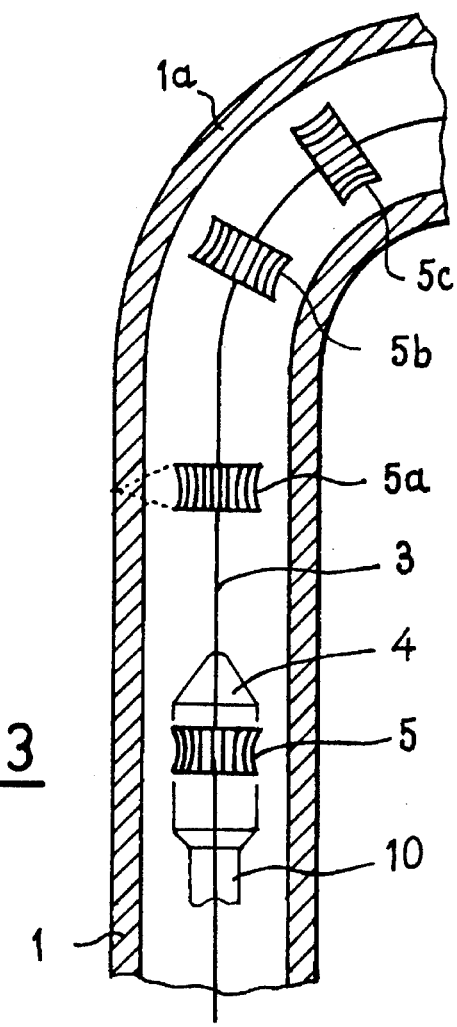
FIG. 3 is an elevation, in cross-section, showing a transducer of an inspection device according to the invention in various positions during its movement inside a tube being inspected.

In FIG. 3 shows the front end portion of the movable portion of the inspection device, comprising a guiding head 4 and a transducer 5 fixed to the end of a movement cable 10, in a first operating position inside a tube 1 comprising a bend 1a and in three successive positions 5a, 5b and 5c during the movement of the device along the axis 3 of the tube 1.

The transducer 5 has the shape of a pellet with a concave lateral surface whose maximum diameter is substantially smaller than the inner diameter of the tube 1 and whose thickness in the axial direction of the tube is small. In this manner, the transducer 5 may easily be moved inside the tube, even in bend zones having a small bend radius such as the zone 1a, because the transducer 5 fixed to the end of the flexible cable 10 is capable of freely taking up successive orientations (positions 5a, 5b, and 5c) inside the tube in its bent portion.

In all the successive positions of the transducer 5, its concave external lateral surface, which constitutes the active surface for emission of ultrasound, as will be explained later, remains constantly directed towards the internal surface of the tube 1.

A transducer according to the invention, the structure of which will be described later and which has the general shape of a flat pellet having a concave lateral surface whose maximum diameter is substantially smaller than the inner diameter of the tube may therefore permit the inspection of a tube from the inside, even when the tube has a small diameter, a long length and bent portions having a small bend radius.

Figure 4A:
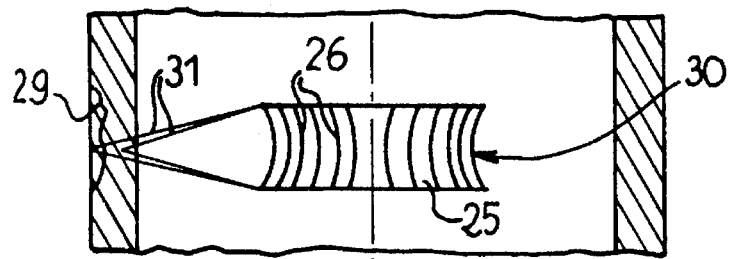
FIGS. 4A, 4B, 4C, 4D are elevations, in cross-section, of several embodiments of transducers of an inspection device according to the invention in position inside a tube to be inspected.
Figure 5:
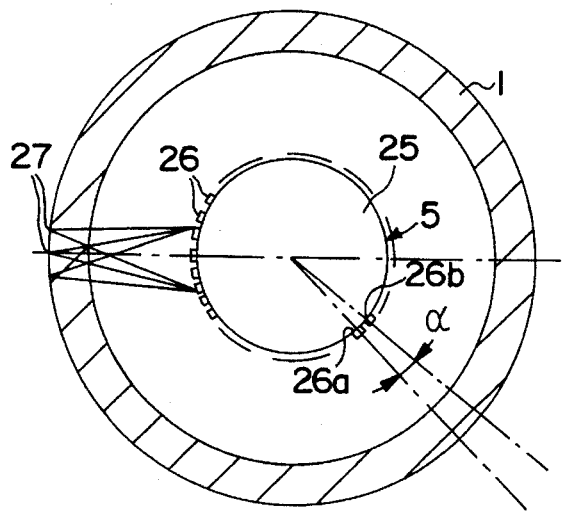
FIG. 5 is a view, in transverse cross-section, of a transducer of an inspection device according to the invention in position inside a tube.
Figure 6:
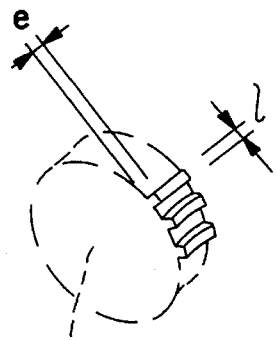
FIG. 6 is a perspective view of a transducer of a device according to the invention comprising a support of cylindrical shape.

Reference will now be made to FIGS. 4A, 5 and 6 in order to describe a transducer of an ultrasonic inspection device according to the invention constructed in the shape of a flat pellet which is symmetrical in revolution and has a concave lateral surface.

The transducer 30 is constituted by a support 25 having the shape of a pellet whose thickness is substantially smaller than its diameter. The support 25 may be constructed, preferably but not necessarily, from an ultrasonic damping material.

The support of the transducer 30 which is symmetrical in revolution has a generatrix defining its external lateral surface which is a curve and whose concavity is directed towards the outside, so that the external lateral surface of the support has a hollow shape.

The piezoelectric elements 26 are constituted by strips having themselves a curved shape corresponding to the shape of the generatrix of the support. These piezoelectric elements are fixed against the external lateral surface of the transducer along the generatrices of the support.

The transducer 30 associated with a movable movement entirety such as shown in FIG. 1 is inserted and axially moved in the tube 1, so that its axis of symmetry is coincident with the axis of the tube.

The geometric shape of the external surface of the transducer, on which surface the curved piezoelectric strips 26 are fixed, enables the ultrasonic waves to be focused in the axial direction of the transducer and of the tube 1 by simple geometric effect, due to the curvature of the surface of the support 25 and of the piezoelectric strips 26. This focusing may be designated by the term "geometric focusing". Thus a focal spot is obtained whose dimension in the axial direction is small.

Moreover, the transducer 30 enables a beam of ultrasonic waves 31 generated by the piezoelectric elements 26 to be variably focused, the focal distance of the beam depending on the curvature of the support and on the excitation sequences of the piezoelectric elements 26.

Thus it is possible to focus the beam into a specified detailed zone of the wall of the tube 1.

In the case of a tube to be inspected having an inner diameter of the order of 20 mm, it is possible to use, advantageously, a support pellet having a maximum diameter of the order of 10 mm and a thickness of the order of 4 mm.

Over the lateral surface of the pellet are fixed piezoelectric elements 26, of very small dimensions, having the shape of curved strips.

The strips 26 are constituted by a crystalline material having piezoelectric properties, i.e., a material which may be excited by an electrical current so as to vibrate and to generate waves having a frequency corresponding to the region of ultrasonic waves.

In the case of a support pellet 25 of 10 mm maximum diameter and 4 mm thickness, the strips 26 have a length about 4 mm, a width l in the circumferential direction of 0.3 to 0.4 mm and a thickness e in the radial direction of 0.1 to 0.3 mm.

Each of the piezoelectric strips 26 is connected via electrical conductors to a switching circuit such as the circuit 7 shown in FIG. 1, enabling the strip to be supplied with electrical excitation current and the measurement currents emitted by the vibrating strip 26 to be collected.

The adaptation of the dimensions of the abovementioned strips, in terms of width and thickness, enables frequencies to be generated greater than those known (5 to 7.5 MHz) since they can reach 10 to 15 MHz. Thus an enhanced resolution of the inspection device is obtained because the wavelengths are considerably decreased in relation to the wavelengths used conventionally for ultrasonic inspection.

The piezoelectric strips 26 are fixed to the outer lateral surface of the pellet 25, in successive positions in the circumferential direction, with substantially constant spacing.

In the case of a support pellet having a diameter of 10 mm and of strips having a width slightly greater than 0.3 mm, it is possible to place eighty piezoelectric strips 26, with a very slight spacing between them, over the totality of the lateral surface of the pellet.

In this case, the angular positions around the axis of the pellet of two successive piezoelectric strips 26a and 26b are separated by an angle $\alpha$ whose value is in the vicinity of 4°.

In FIG. 5, the piezoelectric strips 26a and 26b have been shown in fictitious mutual positions, the angle $\alpha$ having a value substantially greater than 4° so as to clarify the representation.

It is obvious that sequentially supplying the individual piezoelectric strips 26 or groups of strips 26, disposed around the circumference of the pellet 25, makes it possible to scan circumferentially the wall of the tube 1 in which the transducer 5 is disposed so that the axis of the pellet 25 is substantially coincident with the axis of the tube 1.

The focusing of the ultrasonic beams produced by the piezoelectric elements 26 at the outer surface of the tube 1 makes it possible to obtain a focal spot 27 of small extent in the circumferential direction and having successive angular positions around the axis of the tube obtained by scanning which are spaced apart by approximately 4°. Thus a very high resolution is obtained during the scanning of the wall of the tube 1 by the beam of ultrasonic waves.

The combination of the circumferential scanning and the geometric focusing due to the curved shape of the active surface of the transducer makes it possible to obtain the sensitivity necessary for carrying out inspection and defect searching, by virtue of a focal spot of very small dimension.

The waves reflected by possible defects of the wall of the tube 1 are received by the piezoelectric elements 26 which emit electrical signals characteristic of the presence of these defects.

The electrical signals originating from the piezoelectric elements 26 which are analyzed in the processing unit of the inspection device enable the presence of defects in the wall of the tube to be very precisely and very sensitively detected.

It should be noted that circumferential scanning of the wall of the tube 1 is performed solely by electronic means, without having to rotate the transducer 5 inside the tube 1.

Thus it is possible to carry out a complete inspection of the wall of the tube 1 by moving the transducer 5 inside the tube solely by translation in the axial direction of the tube.

The power of resolution of the ultrasonic probe 5 comprising piezoelectric elements over its lateral surface may be adapted to the detail of the defects sought or to the diameter of the tubes to be inspected. It may be increased or decreased, by increasing or reducing the total number of the piezoelectric elements distributed over the lateral surface of the probe and/or by adjusting the curvature of the active surface and of the piezoelectric strips.

It is thus possible to use several hundreds or some tens of piezoelectric elements of very small dimensions disposed successively around the periphery of a support which is symmetrical in revolution and has a curved generatrix. The positions of the successive piezoelectric elements around the axis of the support of the probe, in the case where these piezoelectric elements are uniformly spaced over the periphery of the support, may be spaced apart by an angle of the order of one degree or even less. Where the desired performance for the inspection allows it, the elements may be spaced, for example, by 10° to 20°.

In the case of a transducer used, within the scope of the invention, for inspecting small diameter tubes, sufficient analytical detail and an effective scanning of the wall of the tube will be obtained if the angular distance of two successive positions of piezoelectric elements is less than 10°. In the case where piezoelectric elements are disposed over the entire periphery of a probe which is cylindrical or more generally has a symmetry of revolution, at least seventy two uniformly spaced piezoelectric elements will be disposed around the probe.

However, it is also possible to use transducers which comprise piezoelectric elements over only a portion of their periphery, according to the use to which they are to be put.

In this case, it is possible to use a small number of piezoelectric elements placed over a small portion of the circumference of the probe.

It is possible, for example, to use only three piezoelectric elements disposed over the peripheral surface of a probe support, for the inspection of a longitudinal weld of small width of a rolled and welded tube.

However, in all cases, it is necessary that two successive piezoelectric elements disposed on the periphery of the support be separated by a small angular distance, about 10° or less, so as to obtain the advantages offered by the device according to the invention and, in particular, sufficient analytical detail.

The transducer 30 shown in FIG. 4A makes it possible to detect defects in the wall of the tube 1, such as, for example, a crack 29 located at any location inside the wall of the tube 1, by emission of a beam of ultrasonic waves 31 in the direction of the wall of the tube and focusing of this beam in the vicinity of the external surface of the tube 1.

Circumferential scanning of the wall of the tube and of the defect 29 is obtained by sequential excitation of the piezoelectric elements 26 of the transducer 5.

Figure 4B:
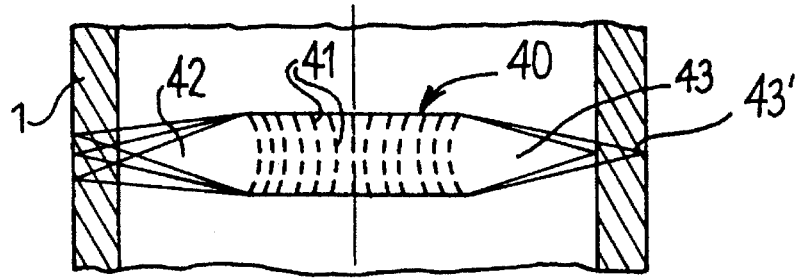

In FIG. 4B shows a transducer 40 which is a variant of the transducer 30 shown in FIG. 4A.

The support of the transducer 40 which has a concave external lateral surface may be constructed in the same manner as the support 25 of the transducer 30.

The continuous curved piezoelectric elements 32 such as used for constituting the transducer 30 are replaced by piezoelectric elements or particles of small dimensions 41 which are placed over the external lateral surface of the support along lines corresponding to generatrix curves.

By sequential excitation of the piezoelectric elements 41, along the generatrix lines, it is possible to obtain local scanning of the wall of the tube 1 in the longitudinal direction, as illustrated by the array of beams of ultrasonic waves 42 showing the successive position of the beam during the scanning.

By acting on the electrical emission and reception signal of a group of piezoelectric elements 41, by means of delay lines, it is also possible to cause the focal distance of the beams of ultrasonic waves to vary, as shown by the beams 43 and 43' which correspond, respectively, to focusing over the internal and external surfaces of the tube. By causing the emission and reception conditions of the piezoelectric elements 41 to vary between the conditions corresponding to the emission and the reception of the beams 43 and 43', it is possible to produce radial focusing. This is designated as dynamic focusing, and enables the entire thickness of the tube wall to be explored.

It is therefore possible, by using transducers of adapted shape, to perform not only circumferential scanning but also scanning in the longitudinal and radial direction of the wall of the tube.

It is thus possible to perform, using only electronic switching means, the scanning and exploration of an entire volume zone of the wall of the tube.

The switching of the various piezoelectric elements may be obtained by a multiplexing device 7, shown in FIG. 2. Such a device makes it possible to transmit a large amount of data sequentially to or from the piezoelectric elements.

Furthermore, it is possible to carry out a programmed excitation of a group of piezoelectric elements so as to obtain an ultrasonic field whose aperture and characteristics are approximately those which would be obtained from a transducer comprising a single piezoelectric pellet.

Figure 4C:
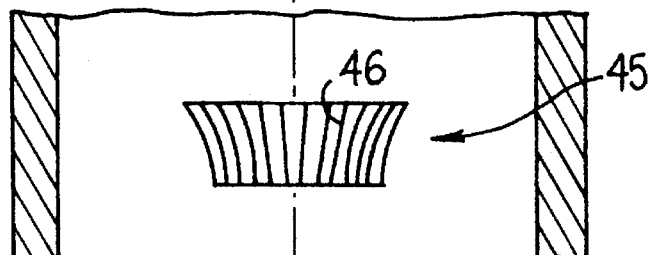

FIG. 4C shows a transducer 45 according to a variant, comprising a support which is symmetrical in revolution, has curved generatrices and a general direction inclined in relation to the axis of symmetry of the support and curved piezoelectric elements 46 having the shape of strips disposed over the external lateral surface of the support along the generatrices of the support.

Figure 4D:
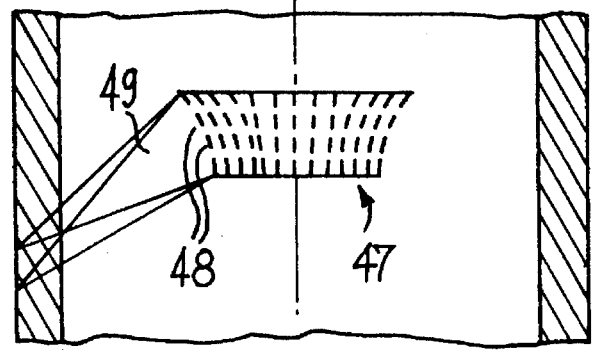

In FIG. 4D shows a transducer 47 which is a variant of the transducer 45, the piezoelectric strips 46 being replaced by piezoelectric elements 48 of small dimensions or particles disposed, along the generatrices of the support of the transducer 47, with a small spacing.

The transducer 47, by supplying the piezoelectric elements 48 sequentially, enables the wall of the tube 1 to be scanned longitudinally by inclined ultrasonic beams 49.

In the case of a transducer such as the transducer 47, it is also possible to obtain, by sequentially exciting the piezoelectric elements disposed along several successive generatrices, an angular deflection of the beam so as to perform an analysis of the wall of the tube in any plane, i.e., a plane different from an axial plane or a transverse plane.

In all cases, the scanning is performed solely by extremely rapid electronic means and without mechanical means.

For the examination of a long length tube, it is therefore simply necessary to move the transducer along the axial direction of the tube.

The rate of scanning and of exploration of the wall of the tube may be very high, which would be impossible where use is made of mechanical scanning means and, in particular, means for rotating the probe about its axis.

When bent or curved portions of the tube, such as shown in FIG. 3, are inspected the device according to the invention enables possible disorientation of the transducer in relation to the axial direction of the tube to be compensated automatically, the axis of the transducer not being exactly directed along the axis of the tube. In fact, the variable intensity of the echoes received by the piezoelectric elements originating from the wall of the tube enables the orientation of the transducer in the tube to be very accurately known and, consequently, the data transmitted by the transducer to be corrected.

Figure 7:
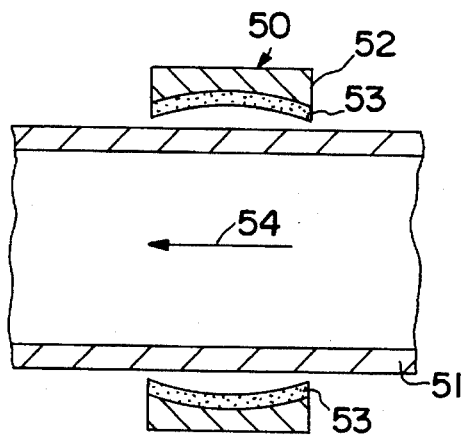
FIG. 7 is a view, in axial cross-section of a transducer of a device according to the invention enabling the wall of tubes to be inspected from the outside.

FIG. 7 shows the transducer 50 of a device according to the invention making it possible to carry out the ultrasonic non-destructive inspection of the wall of a tube 51, from outside the tube.

The transducer 50 comprises a support 52 of annular shape whose inner borehole, curved in the axial direction and concave, has a minimum diameter greater than the diameter of the tube 51 to be inspected.

Curved piezoelectric strips are fixed over the concave inner surface of the annular support 52, along generatrices of this surface of revolution, in angular positions around the axis of the support 52 of the transducer 50 which are staggered with respect to each other by an angle of the order of a few degrees, always 10° or less.

The piezoelectric strips 53 have a length substantially equal to the axial length of the annular support 52.

The non-destructive inspection of the wall of the tube 51 is carried out by performing a relative movement of the transducer 50 in the axial direction 54 in relation to the tube 51. This relative movement may be obtained by moving the tube inside the borehole of the transducer 50 held in a fixed position, or by moving the transducer 50, placed on the periphery of the external surface of the tube 51, in the axial direction.

The piezoelectric elements 53 are thus disposed facing the external surface of the tube 51 so as to emit beams of ultrasonic waves in the direction of the wall of the tube.

A coupling liquid such as water fills the annular space between the transducer 50 and the tube 51 during the inspection, so as to provide the coupling between the piezoelectric elements 53 and the wall of the tube 51.

It is also possible, in some cases, to place the tube in a vessel containing the coupling liquid and to move the transducer along the axis of the tube immersed in the coupling liquid.

A device according to the invention comprising an annular transducer such as the transducer 50 may be used without difficulty in inspecting straight tubes after their manufacture and before they are mounted in an installation such as a heat exchanger.

On the other hand, in the case of bent or curved tubes or in the case of tubes mounted inside the enclosure of a heat exchanger, it is generally preferable to use an inspection device comprising a transducer which is moved in the axial direction inside the tubes to be inspected.

Figure 8:
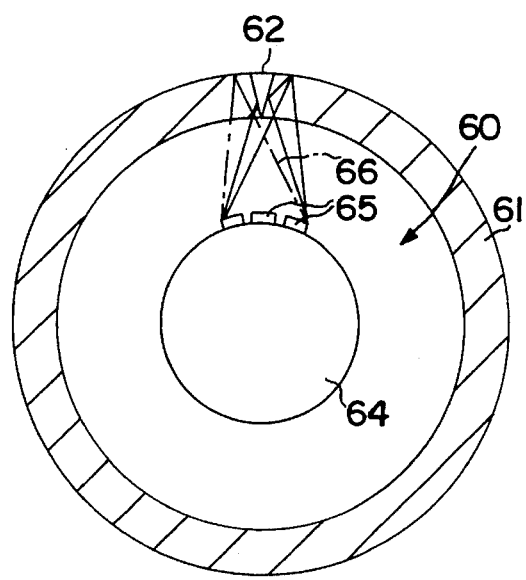
FIG. 8 is a view, in transverse cross-section, of a transducer of an inspection device according to the invention used for the inspection, from the inside of the tube, of a longitudinal weld of a rolled and welded tube.

FIG. 8 shows a tube 61 obtained by rolling a flat product and welding its opposite edges along a rectilinear seam 62.

Shown inside the tube 61 is the transducer 60 of an ultrasonic non-destructive inspection device according to the invention enabling the rectilinear weld seam 62 to be inspected by moving the transducer 60 in the axial direction inside the tube 61.

The transducer 60 comprises a support 64 having the shape of a pellet which is symmetrical in revolution and has curved generatrices, its diameter being substantially smaller than the inner diameter of the tube 61, over the external lateral surface of which piezoelectric elements 65 are disposed.

As in the case of the transducer 5 shown in FIGS. 4A, 5 and 6, these piezoelectric elements 65 are constituted by curved strips of small dimensions made of piezoelectric material, the length of which is substantially equal to the thickness of the support pellet 64.

In the case of a transducer 60 intended for inspecting a peripheral zone of small width of a tube, such as the weld seam 62, the inspection may be carried out by using a small number of piezoelectric elements occupying a restricted portion of the peripheral surface of the cylindrical support 64.

In the case of the inspection of the weld seam 62 of a rolled and welded tube, such as shown in FIG. 8, use is made of a transducer 60 comprising three piezoelectric elements in the form of strips which may be identical to the piezoelectric elements 26 of the transducer 5 which has been described hereinabove.

The three piezoelectric elements 65 are disposed in a peripheral zone of restricted dimension of the support 64, so that the angular positions of these piezoelectric elements 65 around the axis of the pellet 64 are spaced apart by a small angle, of the order of a few degrees, and always 10° or less.

It is thus possible to scan and locally inspect the wall of the tube in the zone of the weld seam 62.

By successive excitation of the three piezoelectric elements 65, the beam of ultrasonic waves 66 produced by the piezoelectric elements is moved so as to scan the zone of the tube comprising the weld seam 62.

Because the piezoelectric elements 65 are narrow and are disposed with a small angular separation around the axis of the pellet, it is possible to obtain a detailed analysis of the zone of the tube comprising the weld 62.

The scanning of the zone to be inspected is carried out solely by electronic means, so that it is not necessary to rotate the transducer about its axis but merely to move it in the axial direction inside the tube in order to carry out the inspection of the weld 62 over its entire length.

Figure 9:
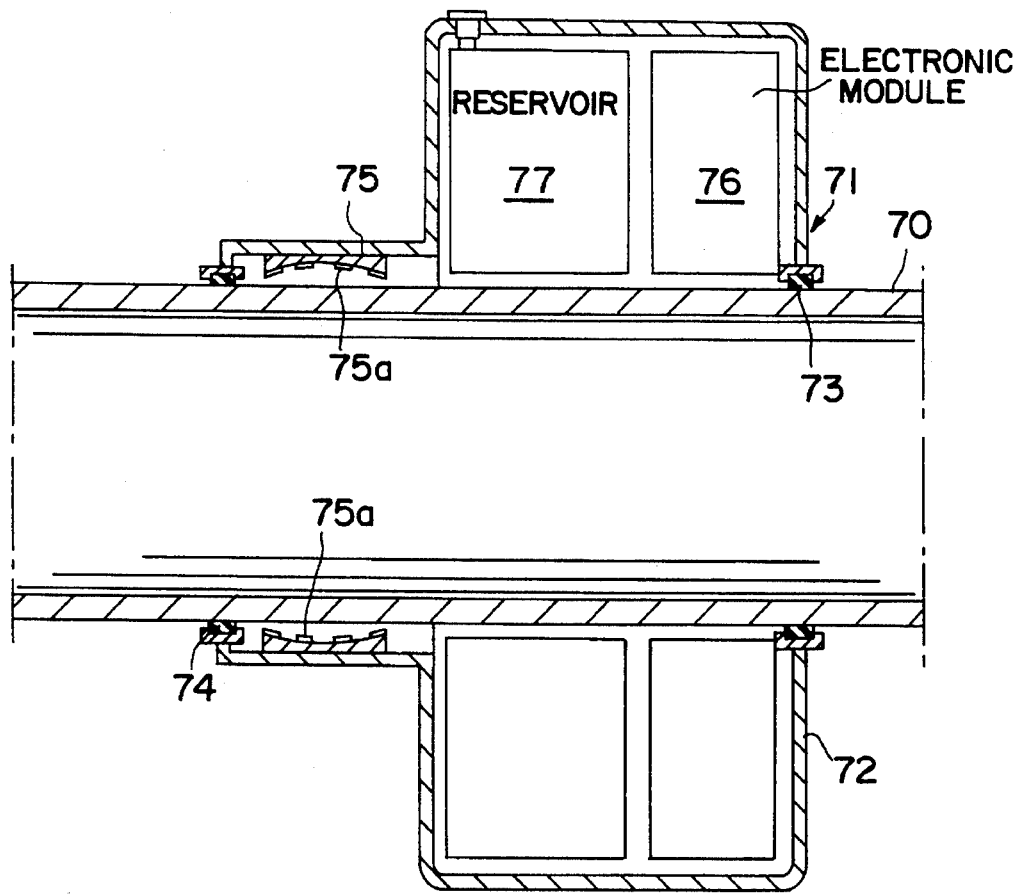
FIG. 9 is a view, in axial cross-section, of a non-destructive inspection device according to the invention used for the inspection of a large diameter tube from the outside.
Figure 10:
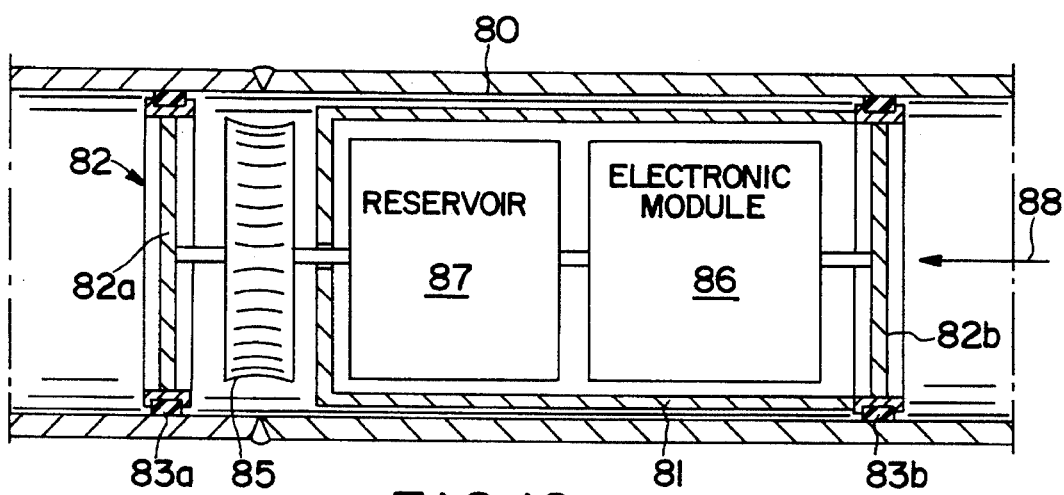
FIG. 10 is a view, in axial cross-section, of a device according to the invention used for inspecting a large diameter tube from the inside.

FIGS. 9 and 10 show that it is also possible to carry out the inspection of the wall of a tube of large diameter and of a weld seam of such a rolled and welded tube from the outside or from the inside of the tube, by using an inspection device according to the invention comprising a transducer which is adapted to the inspection to be carried out and has a support, either of annular shape or of cylindrical shape having curved generatrices, over the surface of which piezoelectric elements of small dimensions are placed in adjacent positions.

In FIG. 9 shows a large diameter tube 70, the non-destructive inspection of which is performed by using a device 71 according to the invention.

The device 71 comprises a housing 72 mounted for movement in the axial direction over the outer surface of the tube 70. Two seals 73 and 74 provide a leaktight junction between the housing 72 and the outer surface of the tube 70. A transducer 75 of annular shape whose internal surface comprises curved generatrices is fixed inside the housing in a disposition which is coaxial in relation to the tube 70 and around the tube. The transducer 75 comprises an active internal surface 75a which is placed facing the tube 70 and over which are disposed curved piezoelectric elements, the concavity of which is directed towards the tube to be inspected, in adjacent angular positions around the axis of the transducer placed along the axis of the tube. The housing 72 also contains one or more electronic modules 76 enabling the piezoelectric elements of the transducer to be supplied sequentially and the signals originating from these piezoelectric elements to be collected and processed.

A reservoir 77 enables a coupling liquid to be introduced into the housing so that the coupling liquid is always present between the surface 75a of the transducer and the tube 70.

The device 81 shown in FIG. 10 enables a large diameter tube 80 to be inspected from the inside. The device 81 comprises a frame 82 constituted by two end-plates 82a and 82b connected to each other and carrying gaskets, respectively 83a and 83b, enabling the volume of the tube 80 between the end-pieces to be closed in a relatively leaktight manner.

The movable device 81 also comprises a transducer which is symmetrical in revolution and has curved generatrices 85, a box constituted by several electronic modules 86 and a reservoir of coupling liquid 87.

The transducer 85 may be constructed in a similar manner to the transducer shown in FIG. 4A. The electronic box 86 enables the piezoelectric elements of the transducer 85 to be supplied and the measurement signals received by the transducer to be collected and processed.

In the case of the device shown in FIG. 9, an appended means (not shown) enables the device 71 to be moved in the axial direction of the tube 70.

In the case of the device shown in FIG. 10, the movement of the movable entirety 81 may be provided by a fluid flowing in the axial direction of the tube 80 or by appended means.

When this is possible, the same fluid is preferably used for providing the movement of the movable entirety 81 and the ultrasonic coupling between the transducer 85 and the wall 80.

The devices as shown in FIGS. 9 and 10 make it possible to inspect the wall of tubes which may be of very long length or of lines such as pipelines with a scan of the entire wall of the tube.

The inspection device according to the invention may be used for carrying out the ultrasonic non-destructive inspection of tubes of long length comprising curves or bent portions having a small bend radius, it being possible for this bend radius to be, for example, of the order of 3 to 5 times the diameter of the tubes and in order to carry out the inspection of structural sections.

The inspections carried out by the device according to the invention can enable defects such as manufacturing defects of tubes or structural sections, a reduction in the thickness of the tubes under the effect of wear, of corrosion or of erosion or even cracks or incipient fractures to be revealed, located and measured.

In all cases, the device according to the invention enables the wall of the tube or of the structural section to be scanned over the surface and in depth, providing detection and very detailed analysis of the defects. This scanning is performed without movement of the probe in relation to the tube other than translational movement in the axial direction of the tube.

For large diameter tubes or structural sections, axial scanning is performed by moving the transducer either by means of the conveyed fluid or by an appended means external or internal to the tube.

The surface and depth scanning of a zone of the wall of the tube or of the structural section may be performed very rapidly by electronic means.

The scanning may be performed in the circumferential direction, in the longitudinal direction and/or in the thickness of the tube; it is also possible to detect and analyze faults in a plane having any orientation in relation to the axis of the tube.

The device according to the invention enables a resolution to be obtained which is adapted to the intended application and to the construction of the transducer. This resolution is greater than that which is obtained with transducers of known type comprising bulky piezoelectric elements whose dimensions are very much greater than the dimensions of the piezoelectric elements of a device according to the invention.

In the case of the device according to the invention, the disposition over a curved support of piezoelectric elements of very small dimensions and the sequential excitation of these piezoelectric elements enable a very good resolution to be obtained and very precisely defined zones of the wall to be scanned solely by electronic means. Furthermore, in the case of the non-destructive inspection devices according to the invention, it is possible to use transducers of very small dimensions, thus enabling bent or curved tubes having a small bend radius to be easily inspected from inside the tubes.

The device according to the invention may therefore be used very easily inspection of the tubes and structural sections during bath manufacture and during operation, for example inside apparatuses such as heat exchangers or steam generators having straight tubes, curved tubes or helically wound tubes.

The device according to the invention makes it possible to inspect very rapidly tubes of very great lengths, for example, a length of 100 m; in fact, the transducer may be moved at a high speed of the order of 12 m/minute in the axial direction of the tube without affecting the quality of the inspection.

In the case of the inspection of tubes of small diameter and more than 10 meters in length, a portion at least of the electronic means used for carrying out the emission and the reception of the signals and the electronic scanning by multiplexing is to be associated with the transducer so as to be moved with the transducer inside the tubes.

Its is possible to use transducers whose support has a shape which is not symmetrical in revolution and over the outer surface of which are fixed piezoelectric elements of small dimensions, which elements are placed in relative positions enabling the surface and the thickness of the wall of a tube or of a structural section to be scanned solely by electronic means.

The means for exciting the piezoelectric elements of the transducer, the means for collecting the measurement signals and the switching means which are associated with them may be of any type known in the art.

The means for guiding and moving the movable entirety of the inspection device comprising the transducer may be constructed in a manner different from that which has been described.

In particular, it is possible to use a pull-push device of any type in order to move a transducer, an element such as a flexible cable providing the support, the movement and the supply of the transducer.

It is also possible to use a known device for moving the frame or the housing carrying the transducer, or even to use the fluid conveyed in a tube.

What is claimed is:

1. A device for ultrasonic non-destructive inspection of an elongate element having a substantially constant cross-section, said device comprising (a) an ultrasonic transducer comprising a support having an active surface generally corresponding in shape to at least one surface of the elongate element, said active surface of said support facing said at least one surface of said elongate element during movements of said transducer, and a plurality of piezoelectric elements fixed to said active surface of said support in adjacent disposition;

(b) means for moving said transducer longitudinally of said elongate element;

(c) means for electrical excitation of said transducer for emission of ultrasonic waves, said excitation means being connected to said piezoelectric elements and controlled so as to produce sequential excitation of said piezoelectric elements, focusing of said ultrasonic waves and scanning of said at least one surface of said elongate element with said ultrasonic waves; and (d) means for collecting and analyzing electrical measurement currents originating from said transducer;

(e) wherein said active surface of said transducer is concave and has, in planes containing an axis of said transducer coincident with a longitudinal axis of said elongate element, cross sections in the form of curves having a concavity directed towards said elongate element, said piezoelectric elements being disposed along some of said curves in such a manner that ultrasonic waves produced by said piezoelectric elements disposed along said curves are focused to produce on the at least one surface of said elongate element a focal spot having a small dimension in the direction of the longitudinal axis of said elongate element.

2. A device according to claim 1, wherein said elongate element is of tubular shape and wherein said active surface of said support is symmetrical in revolution and said curves along which are disposed said piezoelectric elements are generatrices of said active surface having successive positions about said axis of revolution angularly spaced apart by an angle of at most 20°.

3. A device according to claim 2, wherein said transducer is associated with means for axial translational movement of said transducer inside said elongate element of tubular shape.

4. A device according to claim 2, wherein said support of said transducer has an annular shape, said piezoelectric elements being fixed to an inner surface having curved generatrices of said annular support, said inner surface being disposed facing the outer surface of said tubular element which is movable axially relative to said transducer.

5. A device according to claim 2, wherein said transducer comprises piezoelectric elements in the shape of curved strips of piezoelectric material.

6. A device according to claim 2, wherein said piezoelectric elements are constituted by particles of small dimensions having a matrixed disposition over said active surface of said support, the means for electrical excitation and the means for collecting electrical measurement currents having a sequential action controlled electronically in order to scan said at least one surface of the elongate element of tubular shape in a circumferential direction and in a longitudinal direction.

7. A device according to claim 2, wherein said transducer comprises a small number of piezoelectric elements disposed in a small peripheral zone of said active surface of said support of said transducer.

8. A device according to claim 7, wherein said transducer comprises three piezoelectric elements for inspecting and scanning a weld zone of a rolled tube.

9. A device according to claim 1, wherein said piezoelectric elements are particles of small dimensions having a matrixed disposition over said active surface of said support connected to electronic sequential excitation means enabling said at least one surface of said elongate element of tubular shape to be scanned in a circumferential direction, a longitudinal direction and a radial direction.

10. A device according to claim 1, wherein said transducer comprises three to several hundred piezoelectric elements over said active surface of said support.

11. A device according to claim 1, wherein angular positions of said piezoelectric elements disposed successively around the periphery of said active surface of said transducer are separated by an angle of at most 10°.

12. A device according to claim 11, wherein said angular positions of said piezoelectric elements are separated from each other by an angle of between 1° and 5°.

13. A device according to claim 1, wherein said elongate element of tubular shape has an inner diameter of less than 20 mm, and wherein said support of said transducer is constituted by an cylindrical pellet having a concave lateral surface having a diameter of about 10 mm and a thickness of about 4 mm, said piezoelectric elements having a length of about 4 mm, a width between 0.3 and 0.4 mm in a circumferential direction of said support and a thickness between 0.1 and 0.3 mm in a radial direction of said support.

14. A device according to claim 13, wherein said elongate element has a length greater than 10 m, and wherein the means for electrical excitation and the means for collecting and analyzing are associated with said transducer so as to be moved with said transducer inside said elongate element whose inspection is carried out.

15. A device according to claim 1, wherein said support of said transducer comprises curved generatrices having a general direction inclined in relation to the axis of symmetry of said support.

16. A device according to claim 1, wherein said support of said transducer is constructed from a material damping ultrasonic waves.

17. A device according to claim 1, comprising a frame mounted for movement relative to said elongate element to which are fixed an electronic box containing the means for electrical excitation and the means for collecting and analyzing, and a reservoir of coupling liquid for feeding and filling a space between the piezoelectric elements and said at least one surface of said elongate element.

18. A device according to claim 17, wherein said frame is moved, inside the elongate element whose inspection is carried out, by a fluid flowing inside said elongate element, and wherein coupling between said transducer and said elongate element is performed by the flowing fluid.

* * * * *